United States Patent [19]

Barker et al.

[11] Patent Number: 4,552,025
[45] Date of Patent: Nov. 12, 1985

[54] MULTIFUNCTION PROCESSABILITY TESTING METHOD AND APPARATUS

[75] Inventors: Robert I. Barker, Cuyahoga Falls; David P. King, Akron; Henry A. Pawlowski, Seville, all of Ohio

[73] Assignee: Monsanto Company, St. Louis, Mo.

[21] Appl. No.: 529,255

[22] Filed: Sep. 6, 1983

[51] Int. Cl.[4] .............................................. G01N 3/24
[52] U.S. Cl. ........................................ 73/846; 374/47; 73/860
[58] Field of Search ..................... 73/60, 846, 860; 374/47, 48

[56] References Cited

U.S. PATENT DOCUMENTS

| | | | |
|---|---|---|---|
| 1,327,838 | 1/1920 | Naylor | 374/46 |
| 2,037,529 | 4/1936 | Mooney | 73/794 |
| 3,256,741 | 6/1966 | Wise | 73/432 |
| 3,479,858 | 11/1969 | Umeno et al. | 374/48 |
| 3,488,992 | 1/1970 | Veith et al. | 374/48 |
| 3,531,996 | 10/1968 | Harris et al. | 73/432 |
| 3,681,980 | 8/1972 | Decker | 73/794 |
| 3,688,568 | 9/1972 | Karper et al. | 374/47 |
| 4,059,983 | 11/1977 | Fritzsche | 374/47 |
| 4,095,461 | 6/1978 | Starita | 374/47 X |
| 4,343,190 | 8/1982 | Danko et al. | 73/846 |

FOREIGN PATENT DOCUMENTS

1365677 9/1974 United Kingdom ................... 73/60

Primary Examiner—Stewart J. Levy
Assistant Examiner—Joseph W. Roskos
Attorney, Agent, or Firm—Gordon B. Seward

[57] ABSTRACT

A method and apparatus for testing samples of viscoelastic materials are shown, in which the sample is contained under pressure between two dies and the forces involved in rotating one die with respect to the other. The method uses different frequencies of oscillatory rotation at different temperatures. The apparatus uses dies with discontinuous protrusions which overlap each other.

31 Claims, 7 Drawing Figures

MULTIFUNCTION PROCESSABILITY TESTING METHOD AND APPARATUS

BACKGROUND OF THE INVENTION

This invention relates to methods for testing viscoelastic materials to determine their rheological properties and to apparatus for performing such testing. More particularly, this invention relates to methods for applying forces to viscoelastic materials enclosed under pressure and measuring the behavior of the materials, and to apparatus for carrying out these methods.

Prior art methods and apparatus for testing viscoelastic materials include U.S. Pat. No. 2,037,529, relating to the Mooney Plastometer, wherein a plastic material is sheared between rotor and stator and the related forces are measured. In U.S. Pat. No. 3,681,980 a method and apparatus are shown wherein a sample is enclosed in a chamber and subjected to shearing forces by a biconical rotor contained therein. The behavior of a vulcanizing elastomer is thus measured at a fixed temperature, usually a standard temperature for vulcanizing rubber, between 150° and 200° C. U.S. Pat. No. 4,343,190 discloses a method and apparatus for measuring such vulcanization behavior by shearing a rubber sample between two dies, one of which is displaced with respect to the other, and no separate rotor is required.

Other methods and devices are used for testing the behavior of viscoelastic materials which are not in the process of curing or cross-linking. In such cases, the processability of a material may be examined by subjecting it to shearing forces which approximate those forces employed in mixing, shaping or forming operations. Generally, higher shear rates are employed for these so-called processability tests than those used for cure testing, and often the behavior of the material is examined at several different shear rates in order to give a complete picture of the behavior of the material under different process conditions.

Capillary rheometers are often used to measure properties of viscoelastic materials, and can subject a sample to a variety of shear rates so as to evaluate its behavior under processing conditions.

The known methods and apparatus for testing viscoelastic materials are able to test certain aspects of the properties of these materials, but a plurality of different tests are required on widely differing apparatus, and the correlation of the results is often difficult and unreliable. A need exists for a test method and apparatus for viscoelastic materials which could treat a single sample and produce fast, accurate data on the different properties of the viscoelastic materials.

BRIEF SUMMARY OF THE INVENTION

It is an object of this invention to provide a method for evaluating the rheological behavior of viscoelastic materials under a plurality of test conditions. It is another object of this invention to provide apparatus in which a single sample of viscoelastic material can be tested for several purposes in a relatively short time.

These and other objects are accomplished by the instant invention which provides a method for testing a sample of viscoelastic material enclosed under pressure between two opposing, temperature-controlled dies by oscillatory rotation of one die with respect to the other and measurement of the applied force required to deflect the sample or the resultant forces, comprising the steps of holding the sample at a predetermined temperature while measuring one of said forces at two or more oscillatory frequencies, and holding the sample at another, higher, predetermined temperature while measuring one of said forces at one or more oscillatory frequencies.

The instant invention also provides apparatus for measuring the properties of a viscoelastic material which comprises the combination of two opposed dies adapted to contain therebetween a sample of the material to be tested, means biasing the dies towards each other to apply pressure to the sample, means controlling the temperature of the dies, means to rotate one of the dies with respect to the other and means to measure the force required for such rotation as applied torque or reaction torque, wherein each of the dies has at least one annular protrusion extending therefrom towards the other, arranged so that when the dies are biased together an annular protrusion from one die overlaps an annular protrusion from the other die, and each of the protrusions is discontinuous.

It can be seen that the method of the invention is performed in two steps, that the two steps are performed at two different temperatures, and that the step which is performed at the higher temperature is done at at least one frequency, while the step performed at the lower temperature is done at at least two frequencies. Depending on the nature and type of the material being tested, either step can be performed first, but it is found that the low temperature data must be obtained at two or more different frequencies in order to provide adequate information on the rheological properties of the material being tested.

The viscoelastic materials which can be evaluated using the method and apparatus of the invention will usually fall under one of two basic classifications: thermoplastic materials and thermosetting materials. While some of the thermosetting materials can also have thermoplastic properties (in that they have lower viscosities at increased temperatures), for convenience, those materials which are not thermosetting will be termed thermoplastics. Since thermosetting materials harden irreversibly when raised to a given temperature, it is clear that the high temperature step of their testing must be last. Conversely, it is often convenient to measure the properties of a thermoplastic material first at a higher temperature, where the material exists as a fluid "melt", and then at a lower temperature as its resistance to shear increases.

An important category of thermosetting materials is that of vulcanizable elastomers. The method and apparatus of the invention are especially useful for testing vulcanizable elastomers, and provide a means whereby both the processability and the vulcanization behavior of a vulcanizable elastomer can be quickly measured on the same sample and in the same device.

The vulcanization behavior of an elastomer is usually measured (as in the Monsanto Rheometer) at a relatively high temperature and at a single shear rate. A "cure curve" is usually generated, expressing the sample's resistance to shear with time at a given temperature and frequency of oscillation. However, the processability of an elastomer at the lower temperatures used in processing is difficult to characterize using a single shear rate, since the elastomer is usually subjected, in use, to a number of forces over a wide variety of shear rates. Hence, data at a single shear rate could be insufficient or misleading, and the use of multiple shear rates is required to provide a complete picture of the expected behavior of an elastomer throughout all its process steps.

The method and apparatus of the invention provide the ability to evaluate a single sample of viscoelastic material in a plurality of ways within a single apparatus. The evaluation can be rapid and accurate, and is flexible enough to be applicable to a wide variety of materials. Heretofore, testing of a viscoelastic material for such a variety of purposes would require at least two different and separate tests, on at least two different pieces of testing equipment. The invention provides a way, for example, of testing a sample of a rubber compound at typical processing temperatures for its processability, then evaluating its vulcanization behavior at the normal vulcanization temperature using the same sample in the same device. Not only is time and money saved, but one can be certain that the various properties measured apply to the same sample of rubber compound.

The apparatus of the invention is closely related to, and is an improvement on, that described in U.S. Pat. No. 4,343,190, the disclosure of which is hereby incorporated by reference. The instant apparatus improves on the die design, among other features, in that the present invention provides that the protrusions from the die face are discontinuous. The benefits of these discontinuities include, for example, the fact that they permit the escape of any air entrained or entrapped with the sample, thus avoiding erroneous results caused by such air pockets. Also, whatever volatile materials are emitted during the heating of the sample can escape. In addition, the discontinuities can, in some instances, provide additional resistance to sample slippage.

A more complete understanding of the invention can be obtained by reference to the drawings and to the description of the preferred embodiments following.

DETAILED DESCRIPTION OF THE INVENTION

The method of the invention, as set forth above, is for testing a sample of a viscoelastic material. Viscoelastic materials encompass those materials which are neither perfectly elastic nor perfectly Newtonian fluids, but possess some of the attributes of elastic solids and some of fluids. A large variety of rubber and plastic materials are included in this category. Some are thermosetting, as described above, and others purely thermoplastic; those in the latter category can be repeatedly heated to lower their viscosities, whereas thermosetting is an irreversible process.

The sample of the material to be tested is enclosed between two opposing dies, and may be injected into the space between the dies, or placed between parted dies which are then closed to contain the sample. Usually, a slight excess of sample will be charged, and allowed to flow through the area around the seal, ensuring both a full sample cavity and a sealed space.

The sample is subjected to pressure while enclosed between the dies. The pressure is to insure good contact between all die surfaces and the sample, to minimize chances of sample slippage. If the sample contains volatiles which might otherwise form bubbles or voids, the pressure will prevent this from occurring. In any case, the pressure on the sample should be sufficient to enclose it substantially between the dies.

The temperature of the sample is controlled by controlling the die temperature. Sample thickness is usually such that the sample assumes the die temperature throughout in a very short time, with a minimum of variation from point to point. Preferably, the temperature of the dies can be rapidly changed, and will rise at least 1° C. per second from a lower to a higher set temperature.

The dies are designed so as to contain the sample under pressure, provide maximum heat transfer and to apply shear to the sample during the test. Preferably, the dies are as described elsewhere in the specification.

One of the dies, in the method of the invention, is subjected to oscillatory rotation with respect to the other. The rotation is preferably sinusoidal and is preferably performed through an angle of from 0.1 to 10 degrees, at a frequency of from 1 to 10,000 cycles per minute. Where multiple frequencies are used at a given temperature, the frequency can be swept gradually through the desired range, or stepped from one frequency to the next, for preferably, from three to ten set frequencies.

The applied force required to oscillate the one die can be measured, by means of a torque transducer positioned in the drive train. Alternatively, the resultant forces can be measured, such as the reaction torque, which is measured on the other die. Preferably, the normal force can also be measured. Measurement of the reaction torque rather than applied torque is preferred, since the effect of friction anywhere in the drive can thus be avoided. Also, the stiffness of the torque transducer can be designed so that under full torque conditions only a small movement occurs between the upper die and the outer shell, thus minimizing friction or flexure losses at the seal.

Measurement of torque at different points during the oscillation cycle can provide data which give different information about the sample. If torque is measured at the point of maximum displacement the elastic modulus (G') can be calculated. If the torque is measured at zero displacement, the viscous modulus (G") can be calculated. If the complex modulus (G*) is desired, it can be obtained from the maximum torque measurement. The value of tan δ, the tangent of the loss angle can be obtained from the relationship, G" divided by G'. Any or all of these derived quantities, useful in characterizing the material being tested, can be electronically derived during the course of the test, and continuously displayed.

Figure 1:
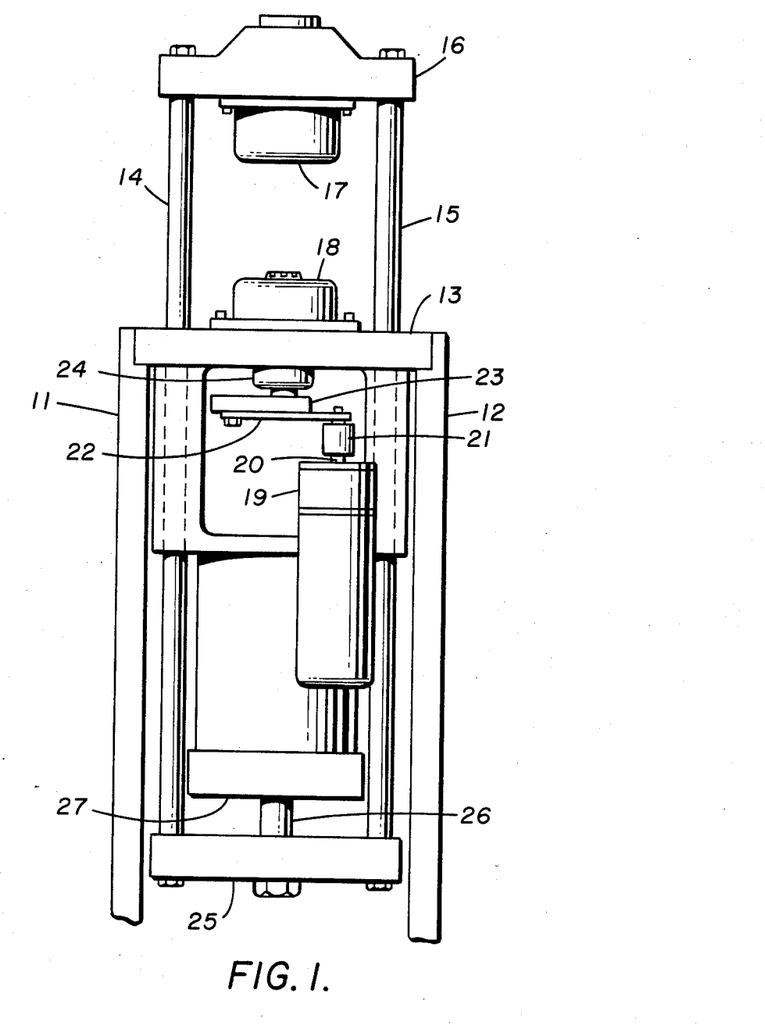
FIG. 1 is a front elevation depicting an overall view of a preferred form of the apparatus.

Referring to FIG. 1, the basic elements of a preferred embodiment of the invention are shown. Left vertical frame member 11 and right vertical frame member 12 are supported by a base (not shown) and, in turn, support horizontal frame member 13. Tie rods 14 and 15 pass through the horizontal frame member and are attached at the top to upper crosshead 15, to which is mounted upper die housing 17. Directly beneath the upper die housing is lower die housing 18, mounted on the horizontal frame member 13.

The drive system for this embodiment includes servo motor 19, mounted below horizontal frame member 13, and connected to the lower die through shaft 20, eccentric 21, connecting arms 22 and 23 to the lower die (not shown), through bearing housing 24.

An air cylinder 27 is mounted below the horizontal frame member, and attached by shaft 26 to lower crosshead 25. The downward motion of air cylinder 27 when actuated thus pulls upper die housing 17 down into contact with lower die housing 18, and applies a normal force on a sample contained between the dies.

Figure 2:
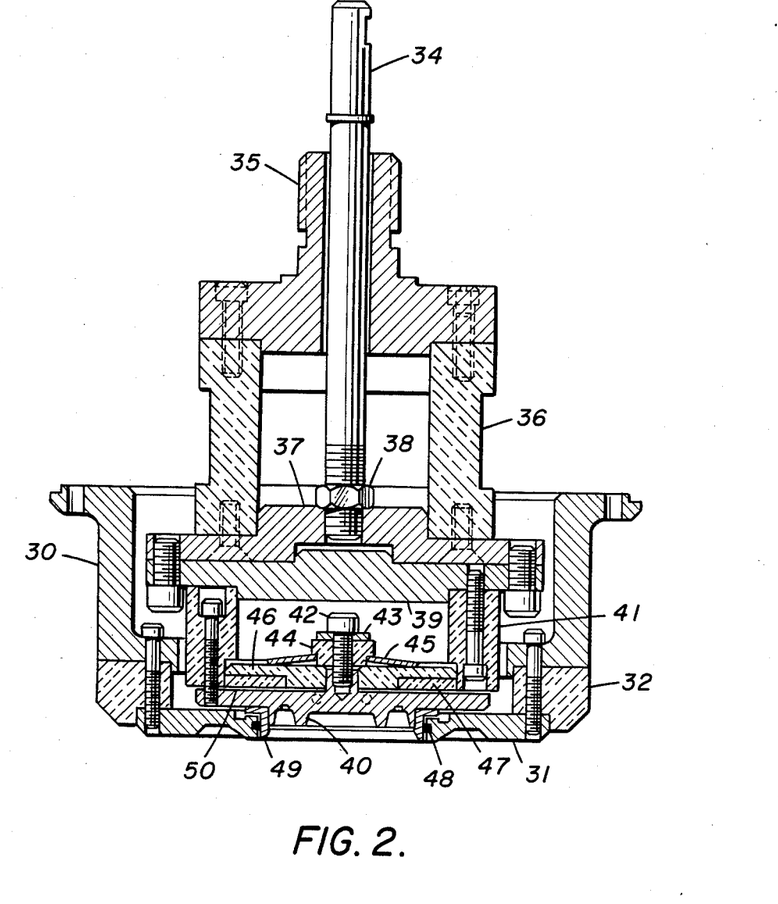
FIG. 2 is a partially sectioned detail view of the upper die assembly.

FIG. 2 shows details of the upper die assembly. Upper die housing 30 is fitted to attach to the bottom of the supper crosshead (not shown). Upper seal plate 31 is attached to the bottom of housing 30 through outer insulator ring 32.

Transducer mount 35 is adapted to be attached to upper crosshead 16, and is bolted to the top of torque/force transducer 36. Rod 34 passes through transducer mount 35 and is attached at its lower end to adapter flange 37 by means of nut 38. The bottom of torque/force transducer 36 is attached to adapter flange 37, which, in turn, is attached to die mounting flange 39.

Upper die 40 is fastened to die mounting flange 39 through inner insulator ring 41. Screw 42 holds washer 43, spring retainer 44 and spring washer 45 on insulator plate 46, all of which, together with heater retainer disc 47, hold heater element 50 in contact with the top of the upper die 40.

An annular groove in upper seal plate 31 holds upper seal 48 in place, and in contact with seal ring 49, which surrounds the lower surface of upper die 40.

Figure 3:
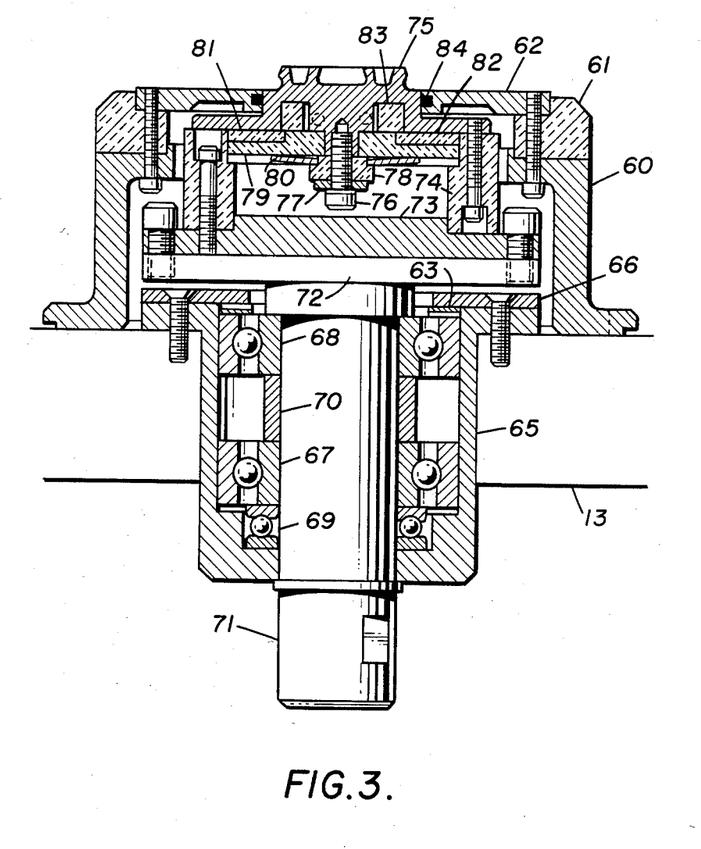
FIG. 3 is a partially sectioned detail view of the lower die assembly.

FIG. 3 shows details of the lower die assembly, which contains some elements which are similar to their counterparts in the upper die assembly. Lower die housing 60 is attached to the top of horizontal frame member 13. Lower seal plate 62 is bolted, through outer insulator ring 61, to housing 60. Bearing housing 65 is also attached to horizontal frame member 13, and is held down by bearing retainer plate 66. Within bearing housing 65 the outer races of lower main bearing 67 and upper main bearing 68 are held by bearing retainer spring 63. Thrust bearing 69 and spacer 70 hold their inner races in place against drive shaft 71.

The upper end of drive shaft 71 is attached to drive plate 72, which in turn is bolted to adapter flange 73. Inner insulator ring 74 is bolted to adapter flange 73, and to lower die 75. In a manner similar to the upper die assembly, screw 76 holds washer 77, spring retainer 78, insulator plate 79, spring washer 80, and heater retainer disc 81 to die 75, holding heater 82 in contact with the lower surface of die 75. Die insert disc 83 fills the cut-out space in die 75.

An annular groove in lower seal plate 62 holds lower seal 84 in contact with a vertical edge of die 75.

Figure 4:
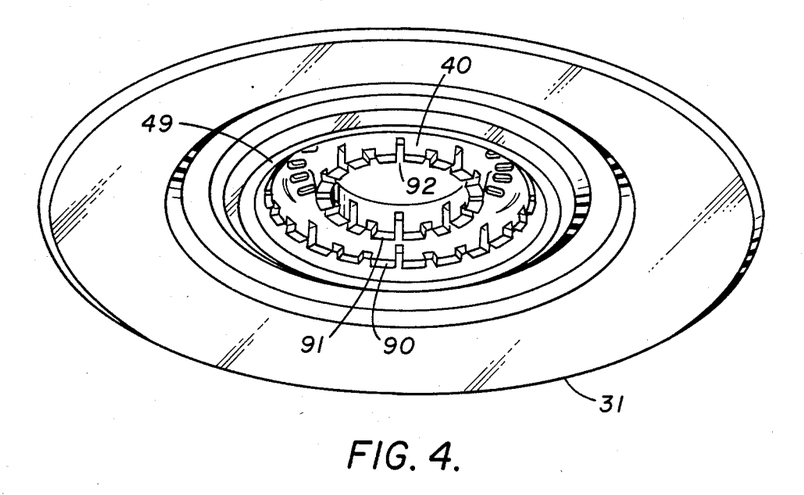
FIG. 4 is a pictorial view showing, in perspective, the upper die, seal ring and seal plate.

FIG. 4 shows a view in perspective of a portion of the upper die assembly. Upper seal plate 31 surrounds seal ring 49 and upper die 40. Outer protrusion 90 and inner protrusion 91 are shown, having a number of slits, one of which is indicated at 92.

Figure 5:
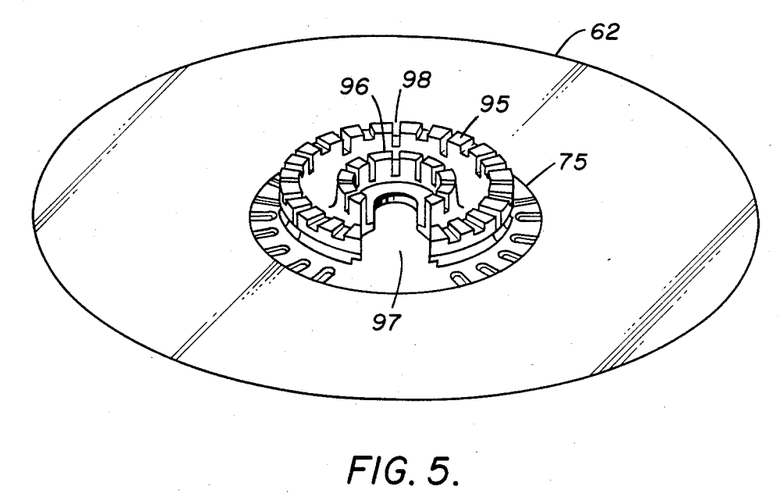
FIG. 5 is a pictorial view showing, in perspective, the lower die and seal plate.

FIG. 5 shows a view in perspective of a portion of the lower die assembly. Lower seal plate 62 surrounds lower die 75, which has outer protrusion 95 and inner protrusion 96, both of which contain numerous slits, one of which is indicated at 98. A slot 97 for sample removal is shown.

Figure 6:
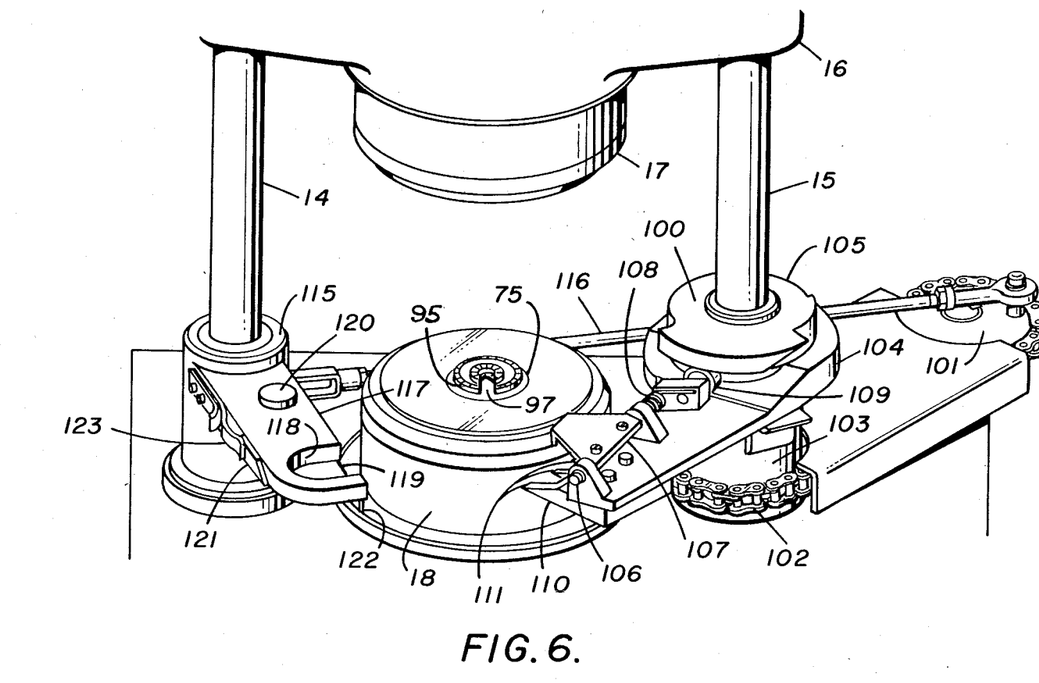
FIG. 6 is a pictorial view of the apparatus showing the automatic sample unloader and loader.

FIG. 6 shows the optional automatic sample loader and unloader mechanisms in position about the lower die housing 18.

The automatic sample unloader, indicated generally at 100, features a drive system (not shown) which turns drive sprocket 101 when actuated by a controller (not shown). Sprocket 101 drives chain 102, which in turn rotates unloader sprocket 103, and unloader arm 104 about tie rod 15 in a clockwise direction. Cam 105 remains stationary. Attached to arm 104 and extending outward from its axis of rotation is unloader shaft 106, which carries upper jaw 107. Spring 108 mounted about shaft 106 urges cam follower 109, eccentrically mounted on shaft 106, against cam 105. Arm 104 also carries lower jaw 110, containing three teeth 111, which opposes upper jaw 107.

The automatic sample loader, indicated generally at 115, is mounted about tie rod 14, and is connected to push rod 116 on one end thereof, the other end of push rod 116 being connected to drive sprocket 101. Loader arm 117 extends horizontally outward from tie rod 14, and has a cut-out portion 118 at its outer end. Mounted on the underside of arm 117 is sample holder plate 119, which is attached to arm 117 at pivot shaft 120. The plate 119 extends across and beneath the cut-out 118, and has vertical flanges 121 and 122, extending upward and downward, respectively, on opposite sides of arm 117. The upwardly extending flange 121 is held against arm 117 by clip spring 123.

In operation, the automatic unloader-loader works in the following sequence: The drive is actuated, rotating drive sprocket 101 and, through chain 102, unloader sprocket 103. The unloader arm 104 is rotated thereby clockwise so that the lower jaw 110 approaches the lower die 75. The middle tooth 111 on jaw 110 slides under the sample just as cam follower 109 reaches the portion of the cam where the follower is released upwardly, rotating shaft 106 under the tension of spring 108 and pivoting the upper jaw 107 so its outer edge grips the sample. Continued rotation of the unloader arm 104 pulls the sample off lower die 75 and out of the way, finally releasing the sample as the cam follower 109 arrives at the sloping portion of the cam 105.

A new sample to be tested in manually placed on the sample holder plate 119 in the loader arm cut-out 118. The rotation of the drive sprocket 101 moves push rod 116 so as to rotate sample loader 115 about tie rod 14 in a counter-clockwise direction until the downward flange 122 of the sample holder plate 119 makes contact with the outer protrusion 95 of lower die 75. Further rotation of sample loader 115 causes sample holder plate 119 to rotate on pivot shaft 120 against the pressure of clip spring 123 and pushes the sample (not shown) off the sample holder plate 119 and into position atop lower die 75. Reverse motion of the push rod 116 then returns loader arm 117 to its original position. When the old sample has been removed and the new sample positioned, air cylinder 27 is actuated, pulling upper crosshead 16 downward by means of the rods 14 and 15, to bring the dies together and enclose the sample for testing.

Figure 7:
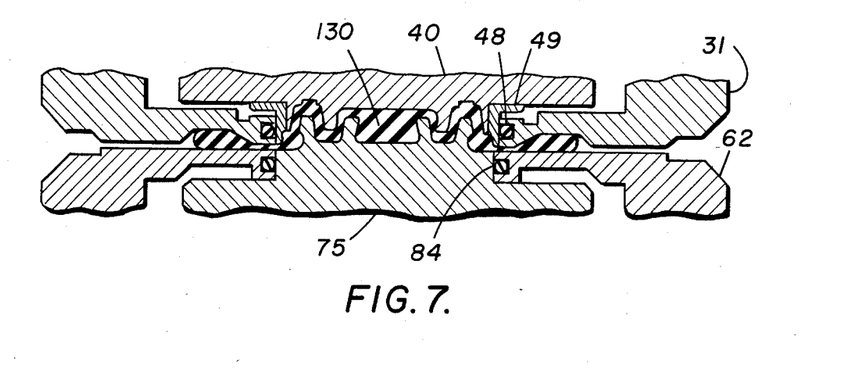
FIG. 7 is a section of a portion of both upper and lower die assemblies in their closed position.

FIG. 7 shows the upper and lower die assemblies, partially, with the dies in the closed position and a sample contained therein. Upper seal plate 31 and lower seal plate 62 are forced together, with the sample 130 contained between upper die 40 and lower die 75, except for the excess sample, which is forced out between the seal plates, and serves to seal them together. Upper seal 48 is in sealing contact with the outer edge of seal ring 49, and lower seal 84 is in sealing contact with an edge of lower die 75.

When the sample has been placed in position on the lower die the air cylinder is activated to drive the upper die assembly downward to enclose the sample in a constant-volume cavity.

The force transducer contained in the torque/force transducer combination detects the closing pressure on the dies and monitors the internal pressure of the cavity continuously during the test. The torque transducer measures the reaction torque on the upper die. The independent outputs of torque and force are fed to respective electronics which deliver high-level analog output signals to the data-handling electronics.

Preferred features of the apparatus of the invention which are not shown in the drawings include temperature control systems, alternative drive systems, and data handling systems.

Temperature control of the dies, and thus of the sample, is preferably accomplished by means of heaters, thermocouples, thermostats and an air blast for cooling. Resistance heaters and thermocouples are located in each die so as to provide uniform heating to all die portions, and a true measure of the die temperature. A thermostat controls current flow to the heaters as needed to maintain the desired temperature. For quick cooling of the dies an air jet can be positioned so as to reduce their temperature as desired.

Although the preferred drive system employs a servo motor for fast response and accurate control, a gearing system coupled to a synchronous drive motor can also be used. Anti-backlash gears are preferably used in this latter system.

The raw data from measurement of forces and temperatures are preferably fed to electronic data handling apparatus which can express derived quantities and parameters, and present them in a visual display. Torque measurements at selected times can be read and optionally plotted on a chart. The nature and type of data handling apparatus will depend on the desired form of the test results.

Although the invention has been illustrated by typical examples and preferred embodiments it is not limited thereto. Changes and modifications of these examples and embodiments herein chosen for purposes of disclosure can be made which do not constitute departure from the spirit and scope of the invention.

The embodiments of the invention in which an exclusive property or privilege is claimed are defined as follows:

1. The method of testing a sample of viscoelastic material enclosed under pressure between two opposing temperature-controlled dies by oscillatory rotation of one die with respect to the other and measurement of the reaction torque comprising the steps of
    A. holding the sample at a predetermined temperature while measuring the reaction torque at two or more oscillatory frequencies, and
    B. holding the sample at another predetermined temperature higher than that of step A while measuring the reaction torque at one or more oscillatory frequencies.

2. The method of claim 1 wherein the viscoelastic material is a thermoplastic polymer.

3. The method of claim 2 wherein step B is performed before step A.

4. The method of claim 1 wherein the viscoelastic material is a thermoset.

5. The method of claim 4 wherein step A is performed before step B.

6. The method of claim 5 wherein the viscoelastic material is a vulcanizable elastomer.

7. The method of claim 6 wherein the vulcanizable elastomer contains a vulcanization system.

8. The method of claim 7 wherein the temperature of step A is substantially below the normal vulcanization temperature of the elastomer and the temperature of step B is about the normal vulcanization temperature of the elastomer.

9. The method of claim 1 wherein the oscillatory rotation is performed at 3 to 10 different fixed frequencies of from 1 to 10,000 cycles per minute during step A.

10. The method of claim 1 wherein the oscillatory rotation is swept through a range of frequencies between 1 to 10,000 cycles per minute during step A.

11. The method of claim 1 wherein the pressure on the sample is sufficient to prevent sample slippage.

12. The method of claim 1 wherein the sample temperature is changed from one predetermined temperature to another at a rate of at least 1° C. per second.

13. The method of claim 1 wherein the force at maximum displacement is measured as torque and the elastic modulus (G') of the sample is calculated.

14. The method of claim 15 wherein the loss tangent (tan $\beta$) is calculated.

15. The method of claim 1 wherein the force at zero displacement is measured as torque and the viscous modulus (G") is also calculated.

16. The method of claim 1 wherein the maximum force is measured as torque and the complex modulus (G*) is calculated.

17. Apparatus for measuring properties of a viscoelastic material comprising, in combination,
    two opposed dies adapted to contain therebetween a sample of the material to be tested,
    means biasing the dies towards each other to apply pressure on the sample,
    means controlling the temperatures of the dies,
    means to rotate one of the dies with respect to the other and
    means to measure the force required for such rotation as applied torque or reaction torque,
    wherein each of the dies has at least one annular protrusion extending therefrom towards the other arranged so that when the dies are biased together an annular protrusion from one die overlaps an annular protrusion from the opposing die, and each of the protrusions is discontinuous.

18. Apparatus of claim 17, wherein each of the protrusions has a plurality of discontinuites.

19. Apparatus of claim 17 wherein at least one of the protrusions comprises an annular row of teeth.

20. Apparatus of claim 19 wherein all of the protrusions comprise annular rows of teeth.

21. Apparatus of claim 17, wherein the means to measure force comprises a torque transducer.

22. Apparatus of claim 17, wherein the biasing the dies towards each other comprises a fluid pressure device.

23. Apparatus of claim 22, wherein the fluid pressure device is an air cylinder.

24. Apparatus of claim 17, wherein the means to rotate the one die is adapted to oscillate the one die.

25. Apparatus of claim 24, wherein the means to measure force is adapted to measure reaction torque on the other die.

26. Apparatus of claim 24 wherein the means to rotate the one die comprises a servo-electric drive.

27. Apparatus of claim 24 further including means to load a sample of material automatically.

28. Apparatus of claim 24 further including means to remove a sample of material automatically.

29. Apparatus of claim 21 further including means for automatic calibration of the torque transducer.

30. Apparatus of claim 24, wherein the means to measure force comprises a torque transducer and a thrust transducer in combination, with means to express both torque and normal force.

31. Apparatus of claim 17 further including air jet means to cool the dies.

* * * * *